United States Patent [19]

Rocco et al.

[11] Patent Number: 5,776,987
[45] Date of Patent: Jul. 7, 1998

[54] PHARMACEUTICAL SUSPENSION FORMULATION

[75] Inventors: William L. Rocco, Reading; Sharon M. Laughlin, Phoenixville, both of Pa.

[73] Assignee: Sanofi Pharmaceuticals, Inc., New York, N.Y.

[21] Appl. No.: 810,560

[22] Filed: Mar. 3, 1997

[51] Int. Cl.$^6$ .......................... A61K 47/08; A61K 47/36
[52] U.S. Cl. .................................. 514/778; 514/314
[58] Field of Search ........................... 424/456; 514/314, 514/778

[56] References Cited

U.S. PATENT DOCUMENTS

| | | | |
|---|---|---|---|
| 5,342,625 | 8/1994 | Hauer et al. | 424/455 |
| 5,420,141 | 5/1995 | Boigegrain et al. | 514/314 |
| 5,633,009 | 5/1997 | Kenealy et al. | 424/448 |

OTHER PUBLICATIONS

Marsh et al Journal of the Assoc. Off. Anal. Chem. vol. 50, No. 2 1967 pp. 457–462.

*Primary Examiner*—Peter F. Kulkosky
*Attorney, Agent, or Firm*—Mary P. Bauman; Michael D. Alexander

[57] ABSTRACT

A pharmaceutical suspension formulation comprising 0.1 to 40% by weight

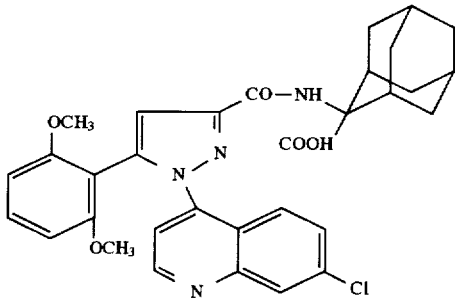

as the active ingredient; 0.1 to 40% by weight Transcutol; 0.1–99% by weight starch; 0–40% by weight polyethylene glycol, NaOH and water, wherein the mole equivalents of NaOH per mole equivalent of active ingredient is from 0.5 to 1.5 is particularly useful for filling hard gelatin capsules.

4 Claims, No Drawings

PHARMACEUTICAL SUSPENSION FORMULATION

BACKGROUND OF THE INVENTION

SR48692 has shown considerable promise as an NT-antagonist for the treatment of psychosis. SR48692 and a method for the preparation thereof are described by Boigegrain et al in U.S. Pat. No. 5,420,141 (Example 186). SR48692 has the structural formula:

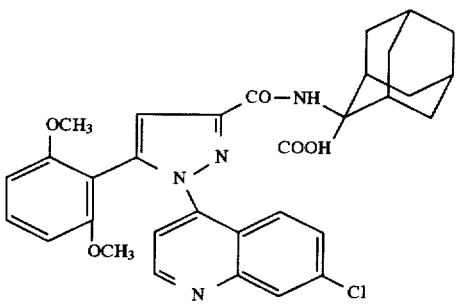

SR48692 has proven to be unusually difficult to formulate into pharmaceutical compositions, due in part to its very low solubility, even in organic solvents.

PCT/US87/02629 discloses a solvent system for enhancing the solubility of an acidic, basic or amphoteric pharmaceutical agent to produce a concentrated solution suitable for soft gelatin capsule filling. The solvent system comprises polyethylene glycol containing 0.2–1.0 mole equivalents of an ionizing agent per mole equivalent of pharmaceutical agent and 1–20% water. Attempts to formulate SR48692 in such a solvent system were not successful.

SUMMARY OF THE INVENTION

We have discovered a solvent system for SR48692 which produces a highly concentrated suspension of the active ingredient suitable for a hard gelatin capsule filling.

More specifically, in accordance with this invention, there is provided a pharmaceutical formulation comprising 0.1 to 40% by weight

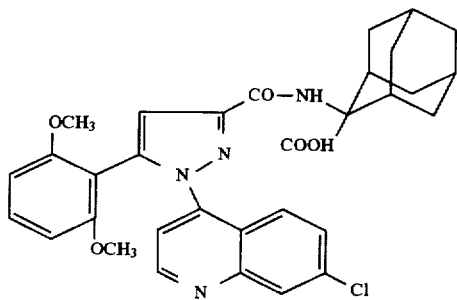

as the active ingredient, 0.1 to 40% by weight Transcutol, 0.1 to 99% by weight starch, NaOH, and $H_2O$.

DESCRIPTION OF PREFERRED EMBODIMENTS

The SR48692 can be present in an amount up to 40%, preferably 0.1–35% and more preferably 0.5–30% by weight.

Transcutol is also known as diethyleneglycol monoethyl ether. The Transcutol is present in an amount of 0.1 to 40%, preferably 0.5 to 35% and most preferably, 1 to 30% by weight of the solid dispersion. Transcutol is commercially available and/or can be prepared by techniques well known to those skilled in the art.

The starch can be present in an amount of 0.1–99% by weight. Starches which have previously been used in pharmaceutical formulations are preferred for use herein. The starch can be pregelatinized, i.e., chemically and/or mechanically processed to rupture all or part of the granules in the presence of water and subsequently dried. Suitable USP/NF starches are described in the Handbook of Pharmaceutical Excipients, Second Edition published jointly by the American Pharmaceutical Association and the Pharmaceutical Society of Great Britain, The Pharmaceutical Press, 1994. A preferred starch is Starch 1500, commercially available from Colorcon.

The suspension can comprise 0.1–20%, preferably 0.5–15% and more preferably 1–13% water. Higher amounts of water tend to soften and/or dissolve the gelatin capsules shells.

The NaOH is present in an amount such that the mole equivalents of NaOH per mole equivalent of SR48692 is from about 0.5 to 1.5.

The polyethylene glycol can be present in amounts of 0–90%, preferably 1–85% and more preferably 2–80% by weight based on the total weight of the formulation.

The polyethylene glycol optionally used herein has an average molecular weight of between about 200–100,000 daltons (hereinafter, all molecular weights are expressed in daltons). Moreover, the molecular weight of polyethylene glycol selected affects the type of solution produced. Polyethylene glycol having an average molecular weight from about 200–800, preferably from about 300–700, and most preferably about 400, produces a hard gelatin capsule fill solution that is a liquid. These low molecular weights are preferred because the PEG is miscible with the Transcutol. High molecular weights may disadvantageously require heat to melt and/or dissolve in the Transcutol. Polyethylene glycol having an average molecular weight from about 800–10,000, preferably from about 2,000–8,000, produces a hard gelatin capsule fill solution that is semisolid, and polyethylene glycol having an average molecular weight between about 10,000–100,000, preferably about 15,000–60,000, produces a hard gelatin capsule fill solution that is solid.

Contemplated equivalents of polyethylene glycol include analogs, such as the polyethylene glycol ethers of various alcohols including but not limited to tetraglycol—the polyethylene glycol ether of tetrahydrofurfuryl alcohol, and copolymers of polyethylene glycol.

The suspensions of this invention can be prepared by adding the SR48692 to the solvent Transcutol, optionally in combination with PEG. The SR48692 is then dissolved by adding aqueous NaOH. The suspension is obtained by adding water which causes a controlled precipitation. Addition of starch to the suspension permits the formulation to be filled into hard gelatin capsules preserving the integrity of the capsule shells.

The following example further illustrates the invention.

EXAMPLE 12 g of PEG 400 and 12 g of diethyleneglycol monoethyl ether were mixed with a magnetic stir plate apparatus at 20° C. Next, 16 g of SR48692 were added along with 4.7 g of aqueous sodium hydroxide (35% w/v). The system was mixed at 20° C. which caused a large proportion of SR48692 to dissolve after 10 minutes. 4 g of purified water was then added and the system was mixed for several hours as a precipitate formed (until a concentrated suspension of drug was achieved). The product was mixed with 12 g of pregelatinized starch with a mortar and pestle to obtain the final formulation. The product was filled into size #0 hard gelatin capsules at 150 mg drug/capsule. After 8 months at room temperature the estimated total impurity level of the product was 0.4%, well within acceptable levels.

Having described the invention with reference to its preferred embodiments, it is to be understood that modifications within the scope of the invention will be apparent to those skilled in the art.

We claim:

1. A pharmaceutical formulation in a highly concentrated suspension form for a hard gelatin capsule filling comprising 0.1 to 40% by weight of the compound having the formula

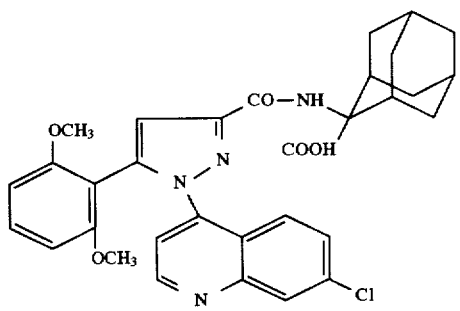

as the active ingredient in combination with a solvent system having improved solubilization effect for said active ingredients; 0.1 to 40% by weight Transcutol; 0.1–99% by weight starch; NaOH and water, wherein the mole equivalents of NaOH per mole equivalent of active ingredient is from 0.5 to 1.5.

2. The formulation of claim 1 wherein the active ingredient is present in an amount of 1 to 30% by weight.

3. The formulation of claim 1 further including polyethylene glycol.

4. The formulation of claim 1 wherein the water is present in an amount from 0.1 to 20% by weight.

* * * * *